United States Patent [19]

Renimel et al.

[11] Patent Number: 5,714,164
[45] Date of Patent: Feb. 3, 1998

[54] METHOD FOR TREATMENT OF ALLERGIC DISORDERS AND COSMETIC COMPOSITIONS USING CUCURBITINE

[75] Inventors: Isabelle Renimel, Trainou; Patrice Andre, Neuvilles Aux Bois, both of France

[73] Assignee: Parfums Christian Dior, Paris, France

[21] Appl. No.: 486,621

[22] Filed: Jun. 7, 1995

Related U.S. Application Data

[63] Continuation of Ser. No. 108,601, Sep. 28, 1993, abandoned.

[30] Foreign Application Priority Data

Feb. 28, 1991 [FR] France ................... 91 02420

[51] Int. Cl.$^6$ .................... A61K 9/127; A61K 31/40
[52] U.S. Cl. .................. 424/450; 424/401; 424/43; 424/45; 424/46; 424/427; 514/359; 514/826; 514/861
[58] Field of Search ................. 424/450, 401, 424/427, 43, 45, 46; 514/359, 826, 861

[56] References Cited

U.S. PATENT DOCUMENTS

| | | | |
|---|---|---|---|
| 4,255,418 | 3/1981 | Bailey | 424/145 |
| 4,421,746 | 12/1983 | Kojima | 424/195 |
| 4,511,559 | 4/1985 | Szendrei | 514/54 |
| 4,883,659 | 11/1989 | Goodman | 424/78 |
| 4,942,153 | 7/1990 | Fernandez | 514/2 |
| 4,980,038 | 12/1990 | Watanabe | 204/157.15 |
| 5,039,516 | 8/1991 | Goodman | 424/59 |
| 5,118,507 | 6/1992 | Clement | 424/401 |
| 5,128,139 | 7/1992 | Byron | 424/450 |
| 5,164,182 | 11/1992 | Meybeck | 424/195.1 |
| 5,165,935 | 11/1992 | Andre | 424/450 |

FOREIGN PATENT DOCUMENTS 2522500   9/1983   France .

OTHER PUBLICATIONS

World Patents Index Latest, AN 87–329987 [47], Derwent Publications Ltd., London, GB, & JP, S, 62234013 (Osaka Yakuhin Kenky), 14 Oct. 1987.
Chemical Abstracts, vol. 82, No. 23, 1975, p. 40, abstract 149446a, Pharmacological (anthelminthic) study of Cucurbita ..., A.E. Gonzalez et al.
Scienta Sinica, vol. X, No. 7, 1961, T.–T. Sun et al, "Chemical studies on cucurbita moschata duch", pp. 852–859.
Journal of the Chemical Society, Chemical Communications, 1973, H.J. Monteiro, "New synthesis of the Amino–acid (+)–Cucurbitine", p. 2.
Chemical and Pharmaceutical Bulletin, vol. 35, No. 9, Sep. 1987, Y. Morimoto et al, "Enzymes and catalysts. II. Pig liver ... ", pp. 3845–3849.
J. Falbe, "Methoden der Organischen Chemie", vol. E5, Georg Thieme Verlag pp. 534–543, 1981.
World Patents Index Latest, 1977, AN 77–39162& [22], Derwent Publications Ltd. 52051033 (Ogawa) 23 Apr. 1977.
World Patents Index Latest, 1987, AN 87–273386 [39], Derwent Publications Ltd. 62087241 (Lion Corp.) 21 Apr. 1987.
World Patents Index Latest, 1987, AN 87–105806 [15], Derwent Publications Ltd. 52051033 (Shiseido) 9 Mar. 1987.
World Patents Index Latest, 1987, AN 87–032891 [05], Derwent Publications Ltd. 62087241 (Shiseido) 19 Dec. 1986.
Price Pathophysiology, Clinical Concepts of Disease Processes, 1986, pp. 36–37.
Webster's New World Dictionary, 1988, p.36.

*Primary Examiner*—Gollamudi S. Kishore
*Attorney, Agent, or Firm*—Sherman and Shalloway

[57] ABSTRACT

The invention relates to the use of cucurbitine or extracts of Cucurbitaceae pips for the preparation of a cosmetic or pharmaceutical, in particular dermatological, composition having antiallergic activity, or for the preparation of cosmetic or pharmaceutical compositions having a reduced risk of being allergenic.

47 Claims, 2 Drawing Sheets

METHOD FOR TREATMENT OF ALLERGIC DISORDERS AND COSMETIC COMPOSITIONS USING CUCURBITINE

This application is a continuation of application Ser. No. 08/108,601, filed Sep. 28, 1993, now abn. which is a 371 of PCT/Fr92/00164 filed Feb. 24, 1992.

The present invention relates essentially to the use of cucurbitine for the preparation of antiallergic cosmetic or pharmaceutical, in particular dermatological, compositions, and to a process involving application thereof.

Cucurbitine, or 3-amino-3-pyrrolidinecarboxylic acid, of the following formula I:

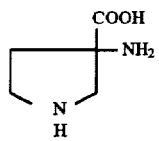

is a natural, water-soluble amino acid found in Cucurbitaceae (see V. H. Mihranian et al., LLOYDIA (1968), 31 (1) 23–29).

Cucurbitine is known as an antiparasitic, especially as an anthelmintic against *Schistosoma japonicum*. (Morimoto Y. et al., Chem. Pharm. Bull. (1987) 35 (9) 3845–3849).

Cucurbitine may be obtained by means of extraction in laevorotatory form, or synthetically in racemic form. Among the various methods of synthesis of cucurbitine, special mention may be made of the synthesis method of H. J. Monteiro, J. Chem. Soc., Chem. Commun. (1973) 2. This method leads to only relatively low yields of racemic cucurbitine. Another synthesis method enables the two optical isomers of cucurbitine to be obtained separately. This is the method of Morimoto et al., Chem. Pharm. Bull. (1987) 35 (9) 3845–3849, which is a stereospecific enzymatic method of synthesis by the use of a pig liver esterase. This method is, however, complicated, and necessitates a relatively large number of steps.

It has now been discovered, unexpectedly, that cucurbitine inhibits the formation of histamine, a well-known mediator of allergies, and hence displays valuable hypohistaminaemic activity. This hypohistaminaemic activity results from the inhibitory action of cucurbitine on histidine decarboxylase, which is the enzyme responsible for the conversion of histidine to histamine. As a result, the administration of cucurbitine contributes to decreasing the histamine concentration in the blood serum and tissues.

This constitutes a considerable technical advance, since allergic manifestations, in particular pulmonary and cutaneous allergies, are nowadays causing many problems for therapists, who have a limited number of active substances at their disposal and, in addition, some of these substances can display side-effects. Thus, a considerable need consequently exists for the development of a new preventive and curative composition for allergies.

Thus, the main objective of the present invention is to solve the technical problem that consists in providing an approach enabling the formation of histamine, a mediating agent in the context of allergic manifestations, to be inhibited in order to enable allergic manifestations to be prevented and treated.

According to another aspect, the main objective of the present invention is to solve the technical problem that consists in providing an approach enabling allergic manifestations to be prevented and treated.

The object of the present invention is also to solve the new technical problem that consists in providing an approach enabling the allergenic potential of cosmetic or pharmaceutical, in particular dermatological, compositions to be decreased.

The object of the present invention is also to solve the new technical problem that consists in providing an approach enabling the synthesis of cucurbitine to be carried out by a simple synthesis process, necessitating a minimum number of steps, in good yields.

The present invention enables all these technical problems to be solved simply, reliably and reproducibly of a cosmetic or pharmaceutical, in particular dermatological, composition having antiallergic activity.

The invention will now be described in greater detail with reference to the following description and preferred embodiments and with the assistance of the accompanying drawings.

Figure 1:
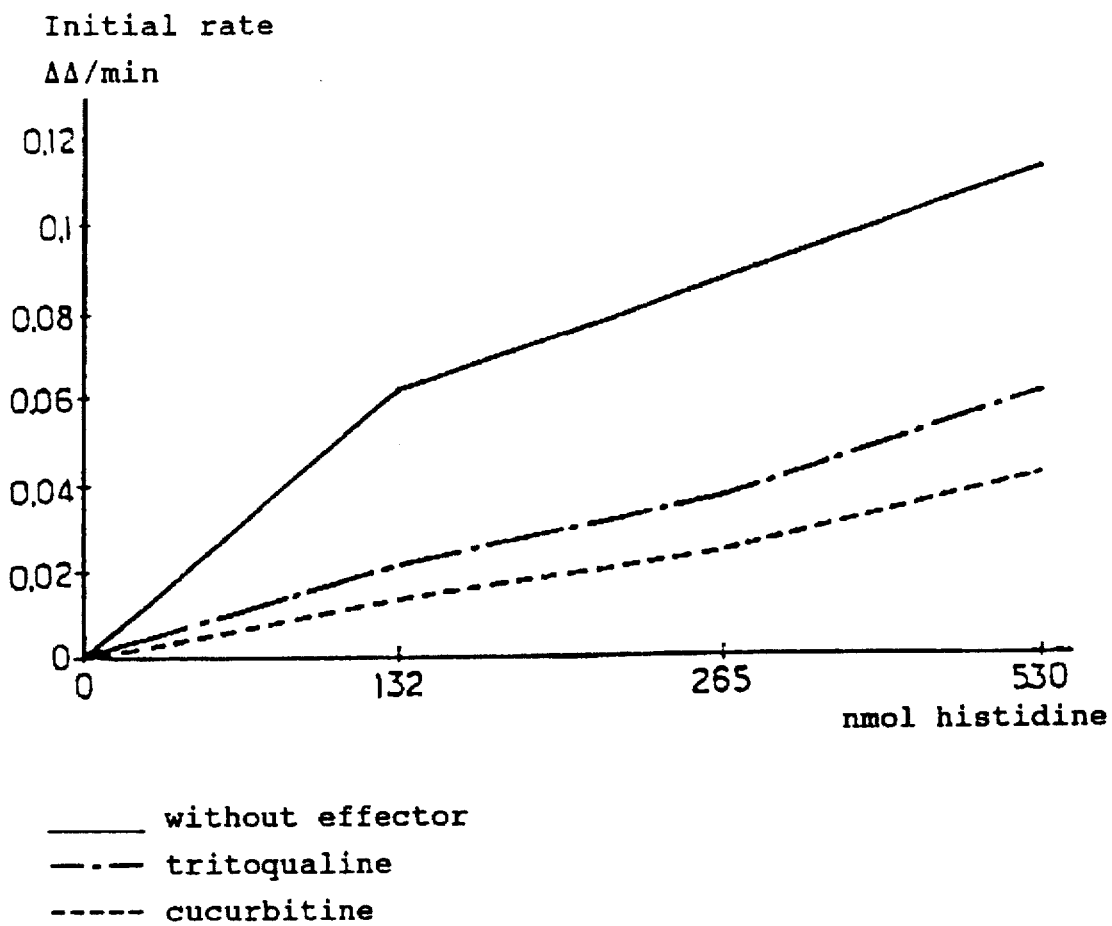
FIG. 1 is a Michaelis curve of the inhibitory activity with respect to enzyme histidine decarboxylase (HDC) for each of control, tritoqualine and cucurbitine in terms of initial rate versus amount histidine.

According to a particular variant of embodiment, the preparation in question is of a cosmetic or pharmaceutical, in particular dermatological, composition intended for the prevention or symptomatic treatment of allergic manifestations, irrespective of their origin and their point of application, in particular the bronchi, skin and eye. Thus, the said composition is intended, in particular, for the prevention or symptomatic treatment of allergic or exercise-induced bronchial asthma, hayfever, spasmodic tracheitis and rhinitis, urticaria, other allergic eruptions, eczema, red blotches or skin irritations of allergic origin, pruritus, Quincke's oedema, allergic conjunctivitis and also allergic reactions of medicinal origin.

In the more particular field of cosmetology, the said composition is intended advantageously for lines of products which are hypoallergenic or for sensitive or irritable skins.

Cucurbitine may be used either in free form, or in the form of one of its cosmetically or pharmaceutically, in particular dermatologically, acceptable salts or esters. The abovementioned salts and esters may be prepared by conventional processes which are well known to a person skilled in the art. Among salts, the mono- and dihydrobromide and the mono- and dihydrochloride may be mentioned. Among esters, the methyl ester and the ethyl ester may be mentioned.

According to an advantageous variant, the abovementioned plant extract containing cucurbitine is an extract of Cucurbitaceae, especially of *Cucurbita maxima* Duch., of *Cucurbita pepo* L. or of *Cucurbita moschata* Duch; preferably, it is an extract of pips or of fruit pulp. As a further preference, it is an extract of Cucurbitaceae pips.

According to a particular variant, the abovementioned plant extract is an extract of Cucurbitaceae fruit pulp containing at least 0.5% by weight of cucurbitine.

According to an advantageous variant of embodiment, cucurbitine or one of its cosmetically or pharmaceutically, in particular dermatologically, acceptable salts or esters is present at a concentration of 0.001% to 10%, and preferably 0.01 to 5%, by weight of the total composition.

According to a second aspect, the present invention also relates to a cosmetic composition, characterized in that it comprises, as active ingredient, cucurbitine or one of its cosmetically acceptable salts or esters, or a plant extract containing it, where appropriate in a cosmetically acceptable excipient, vehicle or carrier.

According to an advantageous variant, the abovementioned plant extract is an extract of Cucurbitaceae as defined above.

According to a preferred variant of embodiment, cucurbitine or one of its salts or esters is present in an amount which is effective for displaying antiallergic activity, especially at a concentration of 0.001% to 10%, and preferably 0.01% to 5%, by weight of the total composition.

According to a third aspect, the present invention relates to a pharmaceutical, in particular dermatological, composition preferably having antiallergic activity, characterized in that it contains cucurbitine or one of its pharmaceutically acceptable salts or esters in an amount which is effective for displaying antiallergic activity, especially for preventing or treating allergic manifestations, in particular in the bronchi, skin and eye, where appropriate in a pharmaceutically acceptable excipient, vehicle or carrier.

According to a variant, the abovementioned cosmetic and pharmaceutical compositions contain an extract of plant origin as defined above.

According to a fourth aspect, the present invention further relates to a process for decreasing the allergenic potential of a cosmetic or pharmaceutical, in particular dermatological, composition, characterized in that an effective amount of cucurbitine, in free form or in the form of one of its cosmetically or pharmaceutically acceptable salts or esters, or of a plant extract containing it as defined above, is incorporated in the said composition so that the final composition presents a reduced risk of being allergenic.

In the context of any one of the above aspects, the preferred weight concentration of cucurbitine, or of its salts or esters, for compositions for topical use, is between 0.001% and 10%, and as a further preference between 0.01% and 5%.

For compositions intended for administration systemically (such as orally, parenterally, rectally, by inhalation, etc.), the cucurbitine concentration is not critical and can reach, for example, 60% of the composition. The dosage in man will generally be between 0.1 mg/kg/day and 20 mg/kg/day, and preferably between 1 mg/kg/day and 15 mg/kg/day.

Moreover, natural cucurbitine, of laevorotatory form, or its salts or esters, is/are generally used. Especially advantageous sources of laevorotatory cucurbitine are the pulp and pips of Cucurbitaceae, especially of the species *Cucurbita pepo L., Cucurbita maxima Duch.* and *Cucurbita moschata Duch.* However, the racemic form of cucurbitine or of its salts or esters may also be used.

Moreover, cucurbitine may be used in pure form, or in the form of extracts, according to any one of the extraction procedures known to a person skilled in the art. Especially advantageous extraction procedures are described in the publication of Valentine H. MIHRANIAN et al. in lloydia 1968, 31, (1) 23–29, which is incorporated herein by reference, especially page 24. This process advantageously provides for treatment of decorticated and defatted Cucurbitaceae seeds with water, which is advantageously heated to at least 50° C. with constant stirring for several hours. Thereafter the mixture is centrifuged, the supernatant is collected and the residues are re-extracted one or more times in a similar manner with several portions of heated water. The supernatant and washings are combined and then treated by adding to an equivalent volume of 85% ethanol to precipitate proteinaceous matter in suspension, and the whole is kept in a refrigerator overnight. The mixture is then centrifuged and the supernatant is collected. The alcohol may be removed by distillation, for example in a rotary evaporator. The aqueous solution may be used as it is, or alternatively passed thereafter through a chromatography column for example of the Dowex 50W-X-8 type, for example measuring 75×2.2.cm. The column is washed with approximately 200 ml of water, and then eluted with 1% aqueous ammonium hydroxide solution until the effluent gives a negative response to the ninhydrin test. The eluate may be evaporated to dryness under reduced pressure, heating where appropriate. The syrupy residue may, again, be used as it is, or alternatively treated again with hot water and advantageously added to an at least equivalent volume of 95% ethanol. Thereafter, the mixture may be acidified dropwise with an acid to bring the pH of the solution to a pH approximately equal to 5, for example with 60% perchloric acid. It may then be placed in a refrigerator for several days to obtain a precipitate of cucurbitine perchlorate. This precipitate can then be dissolved in a few milliliters of water and, where appropriate, passed through a chromatography column, preferably of the Amberlite CG-45 type, for example measuring 20×1.5 cm. Evaporation of the eluate under reduced pressure gives cucurbitine in the substantially pure state.

Thus, the above process makes it possible to obtain either cucurbitine in the pure state, or extracts having variable cucurbitine contents. In the case where cucurbitine is used in the form of an extract of Cucurbitaceae, the cucurbitine content is preferably equal to at least 0.5% by weight of the extract. A preferred source for obtaining cucurbitine consists of the pips of the Cucurbita species such as *Cucurbita pepo L., Cucurbita maxima Duch.* and *Cucurbita moschata Duch.*

According to a fifth aspect, the present invention also covers a process for the treatment of a human being or an animal for preventing or treating allergic manifestations, characterized in that an amount of cucurbitine or one of its pharmaceutically acceptable salts or esters, or of a plant extract containing it as defined above, which is effective for preventing or treating allergic manifestations is administered to the said human being or said animal.

In particular, the abovementioned treatment is applied to the prevention or symptomatic treatment of allergic or exercise-induced bronchial asthma, hayfever, spasmodic tracheitis and rhinitis, urticaria and other allergic eruptions, eczema, red blotches or skin irritations of allergic origin, pruritus, Quincke's oedema, allergic conjunctivitis and also allergic reactions of medicinal origin.

According to a variant of embodiment, cucurbitine or one of its pharmaceutically acceptable salts or esters is administered topically at a concentration preferably of between 0.001% and 10% by weight.

According to another variant of embodiment, cucurbitine or one of its pharmaceutically acceptable salts or esters is administered systemically at a dosage in man of between 0.1 mg/kg/day and 20 mg/kg/day, and preferably between 1 mg/kg/day and 15 mg/kg/day.

The invention further relates to a process for preparing a cosmetic or pharmaceutical, in particular dermatological, composition, characterized in that cucurbitine or one of its cosmetically or pharmaceutically acceptable salts or esters, or a plant extract containing it as defined above, is incorporated in a cosmetically or pharmaceutically acceptable carrier, vehicle or excipient.

According to a variant of embodiment, cucurbitine or one of its cosmetically or pharmaceutically acceptable salts or esters is incorporated in a complete cosmetic or pharmaceutical formulation for decreasing the risk of the latter being allergenic.

According to another variant of embodiment, a composition having antiallergic activity is prepared. Some variants of preparation also result from the foregoing description.

According to a particular embodiment of the invention in the context of any one of the aspects stated above, the abovementioned composition containing cucurbitine or one of its salts or esters, or the abovementioned plant extract, contains, in addition, vesicles of the liposome type. According to a particular variant, the cucurbitine, its salt or ester is at least partially encapsulated in vesicles of the liposome type. The expression "vesicle of the liposome type" is understood to mean both hydrated lamellar lipid phases and lipid vesicles composed of ionic or nonionic amphiphilic lipids. Also, the expression "to incorporate at least partially in vesicles of the liposome type" is understood, in the present description and the claims, to mean that the cucurbitine, its salt or ester is combined with vesicles of the liposome type irrespective of the form of this combination. However, a preferred combination lies in encapsulation of the cucurbitine, its salt or ester in vesicles of the liposome type. However, it is not necessary for the total amount to be incorporated or encapsulated in order to obtain the desired antiallergic effect according to the invention.

It is known that vesicles of the "liposome" type are prepared from lipid substances. The term "lipid" covers all substances comprising a so-called fatty carbon chain, generally containing more than 5 carbon atoms, this substance customarily being designated "lipid".

According to the invention, to form either the lamellar lipid phases or the vesicles of the liposome type, amphiphilic lipids, that is to say lipids consisting of molecules possessing a hydrophilic group which can be equally well ionic or nonionic and a lipophilic group, are used as lipids, these amphiphilic lipids being capable of forming lamellar lipid phases or vesicles of the liposome type in the presence of an aqueous phase.

In particular, among these lipids, there may be mentioned: phospholipids, phosphoaminolipids, glycolipids, polyoxyethylenated fatty alcohols and optionally polyoxyethylenated esters of a polyol. Such substances consist, for example, of an optionally hydrogenated egg or soya bean lecithin, a phosphatidylcholine, a phosphatidylserine, a sphyngomyelin, a cerebroside or an oxyethylenated polyglycerol stearate.

Incorporation of the compounds used according to the present invention in hydrated lamellar lipid phases or in liposomes may be carried out according to known preparation techniques, described, for example, in the document U.S. Pat. No. 4,508,703, and, where appropriate, in combination with the document U.S. Pat. No. 4,621,023.

According to a seventh aspect, the present invention also covers a process for the synthesis of cucurbitine, characterized in that 1-benzyl-3-pyrrolidinone is used as starting material.

According to a particular variant of embodiment of this synthesis process, 1-benzyl-3-pyrrolidinone is treated with an ammoniacal solution of ammonium chloride and of potassium cyanide to obtain (±)-3-amino-1-benzyl-3-cyanopyrrolidine. This compound is then converted by acid or basic hydrolysis to (±)-3-amino-1-benzyl-3-pyrrolidinecarboxylic acid, and lastly a reduction with hydrogen, preferably a catalytic hydrogenolysis, is carried out to obtain (±)-3-amino-3-pyrrolidinecarboxylic acid or (±)-cucurbitine.

According to a preferred variant, the abovementioned ammoniacal solution is an aqueous-alcoholic solution, the alcohol advantageously being isopropanol or methanol.

According to another preferred variant, the abovementioned hydrolysis is performed using 6N aqueous hydrobromic acid solution.

According to yet another variant, the catalytic hydrogenolysis is performed in water under hydrogen at atmospheric pressure in the presence of a catalyst such as palladium on charcoal dispersed in the aqueous reaction medium.

According to a preferred embodiment of the synthesis process, 1-benzyl-3-pyrrolidinone is allowed to react with ammonium chloride and potassium cyanide in a 1:4:4 mole ratio at room temperature for at least 48 h.

According to another particular variant of embodiment, the optical isomers are separated from the racemic mixture according to any separation technique known to a person skilled in the art, and especially via the preparation of diastereoisomers.

The process for the synthesis of cucurbitine according to the invention leads to especially high yields of racemic cucurbitine, on average 2 to 3 times as high as those of the known processes.

Other objects, features and advantages of the present invention will become clearly apparent in the light of the explanatory description which follows and which is given with reference to various examples of preparation of cucurbitine, as well as to various examples reporting the results of pharmacological tests, as well as various examples of cosmetic or pharmaceutical formulation. In the examples, the percentages are given by weight except where otherwise stated.

EXAMPLE 1

Synthesis of Cucurbitine in the Form of a Racemic mixture

The procedure is as follows:

a) Synthesis of (±)-3-amino-1-benzyl-3-cyanopyrrolidine 0.5 g of 1-benzyl-3-pyrrolidinone (2.85 mmol) dissolved in 3 ml of 2-propanol is added to a solution of 0.741 g (11.4 mmol) of potassium cyanide and 0.615 g (11.4 mmol) of ammonium chloride in 7 ml of 28% ammonia solution. The mixture remains at room temperature with stirring for 3 days. The solution is washed with 15 ml of 10% potassium carbonate solution and extracted with dichloromethane (3xc 15 ml). After drying over magnesium sulphate and evaporation of the solvents, an oil (0.475 g) is obtained.

The product is purified on a silica column with solid loading. It is eluted with a 4:2 ether/petroleum ether mixture.

0.402 g of a beige solid is obtained (yield: 70%), the solid consisting of 3-amino-1-benzyl-3-cyanopyrrolidine having the following NMR spectrum:

$^1$HNMR, 300 MHz, CDCl$_3$ 1.8 (broad s, 2H, NH$_2$); 1.97 (ddd, 1H, J$_{4,4'}$=13.4, J$_{4,5}$=8, J$_{4,5'}$=5.4); 2.5 (ddd, 1H, J$_{4,4'}$=8, J$_{4,5}$=8, J$_{4',5'}$=5.4); 2.64 (d, 1H, J$_{2,2'}$=9.4); 3.04 (d, 1H, J$_{2',2}$=9.4); 3.67 (s, 2H, CH$_2$—C$_6$H$_5$); 7.33 (m, 5H, aromatic protons).

b) Synthesis of (±)-3-amino-1-benzyl-3-pyrrolidinecarboxylic acid or (±)-1-benzylcucurbitine The hydrolysis of the compound obtained above may be carried out either in an acid medium or in a basic medium.

Hydrolysis in an acid medium:

0.3 g (1.49 mmol) of 3-amino-1-benzyl-3-cyanopyrrolidine obtained in step a), dissolved in 5 ml of 48% hydrobromic acid, are brought to 40°–50° C. for 4 h. After evaporation of the acid, the product is purified on a silica column. The impurities are removed with $CH_2Cl_2$/MeOH 10% and amino acid is brought off with MeOH/$H_2O$ 15%.

After removal of the methanol, the compound is decolorized with animal charcoal in a minimum amount of aqueous medium in the heated state and then lyophilized.

A dark yellow solid is obtained (yield: 80%), consisting of (±)-3-amino-1-benzyl-3-pyrrolidinecarboxylic acid in the form of a mono- or dihydrobromide having the following NMR spectrum:

$^1$HNMR, 300 MHz, $D_2O$ 2.47–2.69 (m, 1H, $H_4$); 2.75–2.91 (m, 1H, $H_4'$; 3.69–3.94 (m, 3H, $H_5$, $H_{5'}$, $H_2$); 4.12 (d, $J_{2,2'}$=14.2, 1H, $H_{2'}$); 4.58 (2d, J=13.8, 2H, $CH_2$—$CH_5$); 7.62 (s, 5H, aromatic protons).

Hydrolysis in a basic medium:

280 mg (1.39 mmol) of 3-amino-1-benzyl-3-cyanopyrrolidine of step a) are dissolved in 2 ml of ethanol. 5 ml of 10% sodium hydroxide solution are added and the mixture is then brought to reflux for 5 h. After cooling, it is acidified with 48% hydrobromic acid.

The product is purified on a silica column: MeOH/$H_2O$ 10%. The product is decolorized with animal charcoal and then lyophilized. The presence of sodium bromide salts causes a yield of greater than 100% to be obtained.

To remove the salts present, 200 mg of pyrrolidine are taken and brought to pH 8 with 10% sodium hydroxide solution. Duolite Cl⁻ is loaded with 2N hydrobromic acid solution. The salts are removed with distilled water. To detach the pyrrolidine, 0.1N hydrobromic acid solution is used.

After lyophilization, 120 mg of (±)-3-amino-1-benzyl-3-pyrrolidinecarboxylic acid are obtained (yield: 40%).

c) Synthesis of (±)-3-amino-3-pyrrolidinecarboxylic acid or (±)-cucurbitine 300 mg of (±)-3-amino-1-benzyl-3-pyrrolidinecarboxylic acid hydrobromide obtained in step b) are dissolved in 10 ml of water. 0.5 mg of charcoal obtaining 10% of palladium is dispersed, and this suspension is then placed in a hydrogen atmosphere at atmospheric pressure. Stirring is maintained for 18 h. After filtration through filter paper and lyophilization, a yellow solid is obtained (98%), consisting of (±)-3-amino-3-pyrrolidinecarboxylic acid or (±)-cucurbitine having the following NMR spectrum:

$^1$HNMR, 300 MHz, $D_2O$ 2.45 (m, 1H, $H_4$); 2.69 (m, 1H, $H_4'$); 3.61 (d, 1H, $J_{2,2'}$=13.4); 3.67–3.78 (m, 2H, $H_5$, $H_{5'}$); 4 (d, 1H, $J_{2',2}$=13.4).

EXAMPLE 2

Optimization of the Yield of the Synthesis of (±)-cucurbitine

The procedure is as described in Example 1, choosing in step b) hydrolysis with 6N hydrobromic acid, varying, however, the proportion of the reactants of step a).

The yields obtained appear in Table 1 below.

TABLE I

| Number of equivalents Moles | | | Experimental conditions | Yield | |
|---|---|---|---|---|---|
| N.B.P. | $NH_4Cl$ | KCN | of step a) | CN | COOH |
| 1 | 1-1 | 1 | 6 h room temperature | * | <10% |
| 1 | 1-1 | 1 | 4 h 40° ⌈ 50° | * | <10% |
| 1 | 4 | 4 | 4 h 40° ⌈ 50° | * | 20% |
| 1 | 8 | 8 | 4 h 40° ⌋ 50° | * | 20% |
| 1 | 4 | 4 | 48 h room temperature | 66% | 44% |
| 1 | 4 | 4 | 72 h room temperature | 70% | 49% |
| 1 | 4 | 4 | 84 h room temperature | 70% | 56% |

N.B.P.: 1-benzyl-3-pyrrolidinone
*aminonitrile, not isolated
CN: yield of 3-amino-1-benzyl-3-cyanopyrrolidine
COOH—: overall yield of 3-amino-3-pyrrolidinecarboxylic acid The last column of Table I contains the yields of (±)-cucurbitine relative to the starting reactants.

It is observed that the yields are maximal if the reaction is carried out at room temperature for a period exceeding 48 h, using proportions of 1:4:4 between the reactants: 1-benzyl-3-pyrrolidone, ammonium chloride and potassium cyanide.

It was, moreover, observed that hydrolysis by means of hydrobromic acid also led to better yields than when hydrochloric acid at the same concentration is used as hydrolysis agent.

EXAMPLE 3

Separation of the Optical Isomers of Cucurbitine

The separation method, which is known per se, is based on the preparation of diastereoisomeric derivatives by coupling of (±)-cucurbitine with certain optically active reagents after protection of the acid function by esterification and of the cyclic amine function. Each form of these stereoisomers, corresponding to one or other isomer of cucurbitine, will be isolated by chromatography, in particular by high performance liquid chromatography or on a silica column. To regenerate thereafter the two enantiomers of cucurbitine, it suffices to saponify the protecting ester, then to hydrolyse it in order to liberate the acid function, and to liberate the amine function, for example by hydrogenolysis as described in Example 1 in the case where the amine function was protected by substitution with a benzyl radical.

As reagents for the present method, it is possible to use laevorotatory S optical active compounds such as:
(1S)-camphanyl chloride,
(S)-(−)-α-methoxy-α-(trifluoromethyl)phenylacetic acid,
N-(tert-butoxycarbonyl)-L-phenylalanine.

The present example describes the resolution of the racemate of cucurbitine by means of coupling with (1S)-camphanyl chloride.

a) Protection of the acid function of (+)-1-benzylcucurbitine: synthesis of its methyl ester 0.1 g of (±)-1-benzylcucurbitine (0.20 mmol), obtained in step b of Example 1, is added slowly to an ice-cold solution of thionyl chloride (0.28 mmol) and methanol (2 ml). The reaction temperature must not rise above −5° C. The mixture is stirred at 0° C. for 2 h and then brought back to room temperature for two days.

After evaporation, the product is purified on a silica column with solid loading. (Eluent $CH_2Cl_2$/MeOH from 10 to 50%).

A yellow product is obtained in a 70% yield, consisting of (±)-1-benzylcucurbitine methyl ester.

b) Coupling with (1S)-(−)-camphanyl chloride 1 mol of (±)-1-benzylcucurbitine methyl ester, dissolved in 1.5 ml of methylene chloride, is neutralized with 1 mol of triethylamine. 1.1 equivalents of (1S)-(−)-camphanyl chloride are added. The mixture is left stirring at room temperature for 16 h.

The product is purified on a silica column with solid loading (eluent: $CH_2Cl_2$/MeOH 10%).

Separation of the diastereoisomers was performed by HPLC on various columns, in particular $NH_2$-grafted Zorbax®.

EXAMPLE 4

Production of Cucurbitine from *Cucurbita pepo* Pulp

Fresh *Cucurbita pepo* fruits are cut in half, and the pips which can be used for the manufacture of pip extracts are removed. The pulp thereby obtained is ground and lyophilized. The powder is recovered and defatted with petroleum ether in the proportion of 1 l to 100 g of powder. The insoluble matter, which constitutes the desired extract of *Cucurbita pepo* pulp, is recovered by filtration. The proportion of cucurbitine in this extract is assayed by HPLC, and a concentration of 0.03% by weight of cucurbitine is obtained in the defatted dry extract.

The defatted dry extract is then introduced into water, which is heated to approximately 50° C. with stirring until dissolution is complete. An equivalent volume of 95% ethanol is added to precipitate proteinaceous matter in suspension, which is removed by centrifugation. The clear supernatant remaining is then acidified to pH 5.0 with 60% perchloric acid. The solution thus acidified is placed in a refrigerator for at least 2 days to precipitate the cucurbitine perchlorate, which is collected. Cucurbitine may be obtained from this cucurbitine perchlorate in a conventional manner for a person skilled in the art, especially by passage through a cation exchange resin column ($Na^+$ type) and by evaporation of the eluate under reduced pressure.

EXAMPLE 5

Preparation of an Extract of *Cucurbita pepo* Seeds 1.5 kg of previously decorticated *Cucurbita pepo* seeds are ground. The powder obtained is subjected three times to extraction with hexane (3 liters, 2 liters and 1.8 liters) to remove fats. The dried cake obtained is extracted with aqueous hydrochloric acid solution maintained at approximately pH 4. This extraction is carried out in three stages: two at room temperature—approximately 22° C.—and the third at 70° C. At each stage, the time during which the cake-solution is kept in contact with the hydrochloric acid solution (2 liters on the first occasion and 2.5 liters on the following two occasions) is 24 h.

After draining, the solid residue is removed and the aqueous phase is collected, partially evaporated and centrifuged. The centrifugation pellets are washed with distilled water and then discarded. The washing liquors are combined with the centrifugation concentrates.

The aqueous fraction is reconcentrated and then treated with an equal weight of ethanol. A white precipitate forms, which is removed by centrifugation. The aqueous-alcoholic supernatant, which is neutralized, for example, with sodium hydroxide, constitutes an extract containing (−)-cucurbitine, which may be used as it is.

It is also possible to evaporate off the alcohol and then to atomize the aqueous solution obtained, so as to obtain a powder assaying at 3 to 5% of (−)-cucurbitine, depending on the batches of seeds used.

EXAMPLE 6

Preparation of a (−)-cucurbitine-rich Extract of *Cucurbita pepo* Seeds, and Production of Purified (−)-cucurbitine.

A-preparation of an extract of *Cucurbita pepo* seeds

The starting material consists either of Cucurbita seeds, decorticated or otherwise, having a (−)-cucurbitine content of 0.2 to 0.4 per cent by weight, depending on the batch or origin, or of oil-free cakes of Cucurbita seeds having a (−)-cucurbitine content of 0.4 to 0.8 per cent by weight, depending on the batch or origin.

The starting material is preferably ground to approximately 100 micrometers. The ground material is then treated by soaking at room temperature with acidulated water (sulphuric acid at a concentration of 0.1 per cent by weight) at pH 3.5 approximately, for 2 h in the case of ground cakes or up to 16 h in the case of seeds. The amount of acidulated water used is approximately five times the weight of the starting material. The whole is then brought to boiling at atmospheric pressure for 1 h. After cooling to 80° C., the mixture is filtered and then, where appropriate, centrifuged. The aqueous phase obtained is then brought to a temperature of 80° C. to 90° C. and thereafter microfiltered through a 0.5 micrometer filter. A juice assaying at approximately 10 g of dry matter per liter is thereby obtained.

This juice then undergoes a thermal preconcentration under a partial vacuum to a concentration of approximately 250 g/l of dry matter. This preconcentrate is thereafter placed at 4° C. for 48 h, then undergoes a further concentration under reduced pressure to 500 g of dry matter per liter, and is again left standing at 4° C. for 48 h. These operations are followed by filtration through a filter press. An extract containing from 40 to 50% of dry matter and assaying at between 1 and 2% of (−)-cucurbitine is thereby obtained. The yields are approximately 200 l of extract per tonne of starting material.

B-Production of purified (−)-cucurbitine

The abovementioned preconcentrate, assaying at 250 g to 300 g of dry matter per liter, is neutralized with sodium hydroxide to obtain a pH of 7.5. The mixture is filtered through a filter press and the filtrate is then passed through a cation exchange resin (of the $Na^+$ type). Elution is performed using ammonia solution. After thermal concentration of the eluate under a partial vacuum, a syrup is obtained, the dry matter of which contains approximately 50% by weight of (−)-cucurbitine. If so desired, this syrup may by lyophilized. For this purpose, it will advantageously be mixed with a neutral powdery carrier such as talc.

EXAMPLE 7

Demonstration of the Inhibitory Activity of Cucurbitine with Respect to Histamine Formation 1-A by an Enzymatic Test This test is based on the inhibitory action of cucurbitine on the enzyme histidine decarboxylase (HDC), which converts histidine to histamine, in comparison with that of tritoqualine, which is a known inhibitor of HDC (see Carpi C., Maggi G. C. Bull. Soc Ital. Sper. 1968, 44 (6 543–4) and which is used therapeutically as a hypohistaminaemic agent under the name Hypostamine®.

The inhibitory activity with respect to HDC may be readily assessed by a colorimetric assay on the basis of the following chemical reaction:

Colorimetric assay

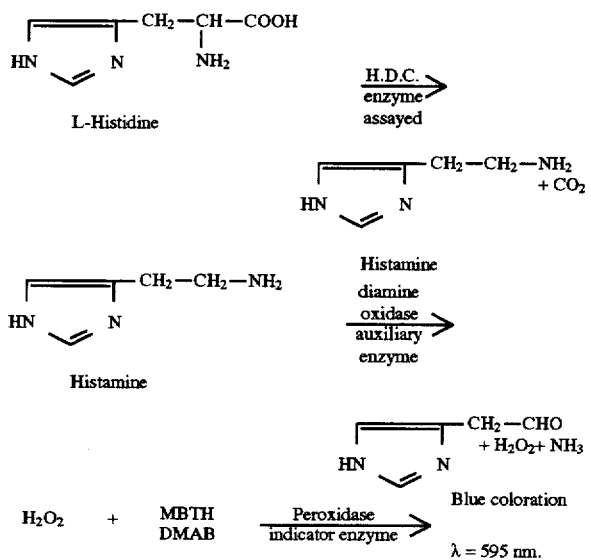

MBTH=3-methyl-2-benzothiazolinonehydrozone
DMA=3-(dimethylamino)benzoic acid

In practice, it is observed that the formation of the blue coloration is proportional to the concentration of histidine consumed. It has thus been possible to define initial rates of reaction and to plot so-called Mickaelis curves as described in Fundamentals of Enzymology, 2nd Ed. Oxford Univ. Press, 1989.

The initial rate is expressed as a change in absorbance per minute.

The results obtained with various initial concentrations of histidine, namely 132 nmol, 265 nmol and 530 nmol, respectively without effector, with tritoqualine as a known HDC inhibitor and with cucurbitine in racemic form as inhibitor according to the invention, are recorded in Table II below, and form the subject of the Mickaelis curve which is the subject of FIG. 1.

TABLE II

| Histidine | 132 nmol | 265 nmol | 530 nmol |
|---|---|---|---|
| Without effector | 0.062 | 0.089 | 0.1132 |
| Tritoqualine (prior art) | 0.021 | 0.0374 | 0.0604 |
| Cucurbitine (invention) | 0.013 | 0.0242 | 0.042 |

It emerges clearly from Table II and from the Mickaelis curve which is the subject of FIG. 1 that cucurbitine is a much more potent HDC inhibitor than tritoqualine, constituting an altogether surprising result for a person skilled in the art.

1-B by a RIA assay

The antihistaminic activity of cucurbitine may also be demonstrated by a radioimmunological assay (Radio Immuno Assay or "RIA") in the following manner.

This assay takes place by assaying the histamine produced directly under the action of the enzyme HDC, by the RIA method which is well known to a person skilled in the art and described, in particular, in the directions for use of an assay kit called HISTAMINE Radioimmunoassay kit (Cat.≠1302) marketed by the company IMMUNOTECH (Marseilles-France).

The amount of histamine liberated (in nanomoles) for a $16 \times 10^{-3}$ molar concentration of histidine in a phosphate buffer at pH 6.3 is assayed over time, respectively without effector, with tritoqualine as effector for comparison and with synthetic racemic cucurbitine as antihistaminic agent according to the invention. Tritoqualine and cucurbitine are used at a concentration of $2 \times 10^{-3}$ molar.

Figure 2:
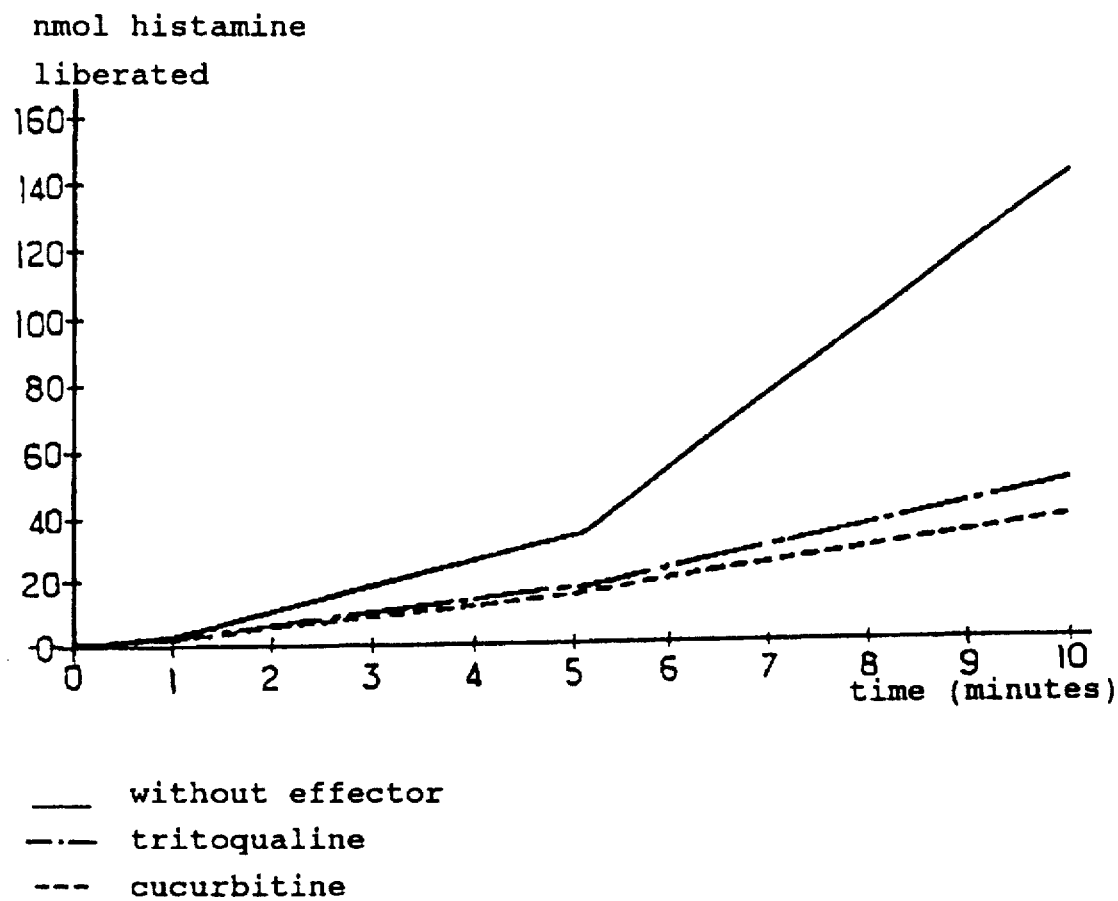
FIG. 2 is a graphic plot of an RIA assay for antihistaminic activity of cucurbitine, according to this invention, in comparison to that of tritoqualine and a control.

The results obtained, expressed as nanomoles of histidine liberated, are recorded in Table III below and form the subject of the curve of FIG. 2, where the number of nanomoles of histamine liberated has been shown as ordinates and the time expressed in minutes as abscissae. The curve without effector is plotted as a continuous line, the curve obtained with tritoqualine is plotted as a chain-dotted line and the curve obtained with cucurbitine is plotted as a dotted line.

TABLE III

| Time | 5 min** | 10 min** | % I* (at 5 min) | % I* (at 10 min) |
|---|---|---|---|---|
| Without effector | 32.66 | 140.79 | 0 | 0 |
| Tritoqualine | 16.48 | 49.27 | 49 | 65 |
| Cucurbitine | 14.85 | 38.29 | 55 | 73 |

*I = Inhibition
**nanomoles of histamine liberated

It is clearly seen from Table III that the amount of histamine liberated is markedly lower in the presence of cucurbitine.

The results obtained by the RIA method hence confirm that cucurbitine has a markedly more potent inhibitory activity with respect to histamine formation than tritoqualine after a few minutes.

Various examples of formulation of cosmetic or pharmaceutical, in particular dermatological, compositions according to the invention are as follows:

EXAMPLE 8

Per tablet for oral administration:

| Per tablet for oral administration: | |
|---|---|
| (±)-cucurbitine | 100 mg |
| starch | 38 mg |
| lactose | 75 mg |
| talc | 10 mg |
| other excipients for tablets (including magnesium stearate) qs | 250 mg |

Indications: preventive and curative treatment of allergic manifestations, in particular cutaneous and respiratory manifestations.

Dosage: 1 to 10 tablets per day for adults. Decrease the dosage by 2 for children up to 15 years of age.

EXAMPLE 9

Powder for Aerosol

Per 100 g in a pressurized can:

| Per 100 g in a pressurized can: | |
|---|---|
| (±)-cucurbitine | 3 g |
| mannitol | 1 g |
| propellent gases | 96 g |

Indications: preventive and curative treatment of all respiratory allergic manifestations such as bronchial asthma and asthmoid bronchitis.

Dosage: intrabronchial administration, at the rate of 4 to 6 inhalations per day on average.

| Example 10<br>Demulcent emulsion for sensitive skin | |
|---|---|
| pip extract according to Example 5 assaying at 3% of (−)-cucurbitine | 10 g |
| conventional cosmetic emulsion for sensitive skins (fatty alcohols, mineral oil, isopropyl palmitate, glycerol, gelling agent, preservatives, fragrances, water) qs | 100 g |
| Example 11<br>Hypoallergenic make-up foundation | |
| extract of Cucurbita pepo pulp, fortified with (−)-cucurbitine, according to Example 4, having a content of 1% of (−)-cucurbitine | 10 g |
| conventional make-up foundation compoisiton (fatty esters, squalane, soya bean lecithin, volatile silicone, propylene glycol, xanthan gum, sunscreen agent, pigments, preservatives, fragrance, water) qs | 100 g |

EXAMPLE 12

Anti-irritant Mascara

| | |
|---|---|
| (±)-cucurbitine | 1.0 g |
| ultramarine blue | 9.0 g |
| hexadecyl alcohol | 7.4 g |
| propylene glycol | 9.0 g |
| stearic acid | 11.3 g |
| glycerol monostearate | 4.4 g |
| triethylamine | 3.6 g |
| preservative | 0.3 g |
| water qs | 100 g |

We claim:

1. A method for treating histamine dependent allergic manifestations in a human being or an animal in need thereof, which comprises administering to the human being or animal a composition containing a histamine dependent allergy treating agent which consists essentially of an histamine inhibiting effective amount of Cucurbitine.

2. The method of claim 1, wherein Cucurbitine is selected from the group consisting of a pharmaceutically or cosmetically acceptable salt or ester of Cucurbitine.

3. The method of claim 1, wherein Cucurbitine is present in laevorotatory form.

4. The method of claim 1, comprising administering said composition containing from 0.001% to 10% by weight of Cucurbitine based on the total composition.

5. The method of claim 1, comprising administering said composition containing from 0.01% to 10% by weight of Cucurbitine based on the total composition.

6. The method of claim 1, comprising administering said composition containing from 0.01% to 5% by weight of Cucurbitine based on the total composition.

7. The method of claim 1, comprising administering Cucurbitine at least in part encapsulated in liposome vesicles.

8. The method of claim 1, wherein said Cucurbitine is selected from the group consisting of (−)Cucurbitine, Cucurbitine mono hydrobromide, Cucurbitine dihydrobromide, Cucurbitine mono hydrochloride, Cucurbitine dihydrochloride, Cucurbitine methyl ester and Cucurbitine ethyl ester.

9. The method of claim 1, comprising administering said composition containing Cucurbitine as an aerosol.

10. A method for decreasing the histamine dependent allergenic potential of a cosmetic or pharmaceutical composition, comprising incorporating in said composition an effective amount of Cucurbitine in at least substantially pure form, so that the final composition displays a reduced risk of being allergenic.

11. The method of claim 10, wherein Cucurbitine is selected from the group consisting of pharmaceutically or cosmetically acceptable salt or ester of Cucurbitine.

12. The method of claim 10, wherein Cucurbitine is present in laevorotatory form.

13. The method of claim 10, comprising incorporating Cucurbitine in said composition in an amount of from 0.001% to 10% by weight of the total composition.

14. The method of claim 10, comprising incorporating Cucurbitine in said composition in an amount of from 0.01% to 10% by weight of the total composition.

15. The method of claim 10, comprising incorporating Cucurbitine in said composition in an amount of from about 0.01% to 5% by weight of the total composition.

16. The method of claim 10, comprising administering Cucurbitine at least in part encapsulated in liposome vesicles.

17. The method of claim 10, wherein said Cucurbitine is selected from the groups consisting of (−)Cucurbitine, Cucurbitine mono hydrobromide, Cucurbitine dihydrobromide, Cucurbitine mono hydrochloride, Cucurbitine dihydrochloride, Cucurbitine methyl ester and Cucurbitine ethyl ester.

18. A method for decreasing histamine concentration in the blood serum and tissues of a person in need thereof comprising systemically administering to said person from about 0.1 to 20 mg/kg/day of at least substantially pure Cucurbitine.

19. The method of claim 18, wherein Cucurbitine is selected from the group consisting of a pharmaceutically acceptable salt or ester of Cucurbitine.

20. The method of claim 18, wherein Cucurbitine is present in laevorotatory form.

21. The method of claim 18, comprising systemically administering Cucurbitine in a composition comprising from 0.001% to 10% by weight of said at least substantially pure Cucurbitine based on the total composition.

22. The method of claim 18, comprising systemically administering Cucurbitine in a composition comprising from 0.01% to 5% by weight of said at least substantially pure Cucurbitine based on the total composition.

23. The method of claim 18, comprising systemically administering Cucurbitine in a composition comprising from 0.01% to 5% by weight of said at least substantially pure Cucurbitine based on the total composition.

24. The method of claim 18, comprising systemically administering Cucurbitine at least in part encapsulated in liposome vesicles.

25. The method of claim 19, wherein said Cucurbitine is selected from the group consisting of (−)Cucurbitine, Cucurbitine mono hydrobromide, Cucurbitine dihydrobromide, Cucurbitine mono hydrochloride, Cucurbitine dihydrochloride, Cucurbitine methyl ester and Cucurbitine ethyl ester.

26. The method of claim 18, comprising systemically administering Cucurbitine as an aerosol.

27. A method of treating histamine dependent respiratory allergic disorders of a human being or an animal comprising administering to said human being or animal at least substantially pure Cucurbitine in an amount which is effective for treating said respiratory allergic disorders.

28. The method of claim 27, wherein said respiratory allergic disorders are selected from the group consisting of bronchial asthma and asthmoid bronchitis.

29. The method of claim 27, wherein Cucurbitine is selected from the group consisting of a pharmaceutically acceptable salt or ester of Cucurbitine.

30. The method of claim 27, wherein Cucurbitine is present in laevorotatory form.

31. The method of claim 29, comprising administering Cucurbitine in a composition comprising from 0.001% to 10% by weight of said at least substantially pure Cucurbitine based on the total composition.

32. The method of claim 27, comprising administering Cucurbitine in a composition comprising from 0.01% to 10% by weight of said at least substantially pure Cucurbitine based on the total composition.

33. The method of claim 27, comprising administering Cucurbitine in a composition comprising from 0.01% to 5% by weight of said at least substantially pure Cucurbitine based on the total composition.

34. The method of claim 27, comprising administering Cucurbitine at least in part encapsulated in liposome vesicles.

35. The method of claim 27, wherein said cucurbitine is selected from the group consisting of (−)Cucurbitine, Cucurbitine mono hydrobromide, Cucurbitine dihydrobromide, Cucurbitine mono hydrochloride, Cucurbitine dihydrochloride, Cucurbitine methyl ester and Cucurbitine ethyl ester.

36. The method of claim 27, comprising administering Cucurbitine as an aerosol.

37. A method for the cosmetic treatment of skin with a histamine dependent allergic tendency, comprising applying to said skin a cosmetic composition containing at least substantially pure Cucurbitine.

38. The method of claim 37, wherein Cucurbitine is selected from the group consisting of a cosmetically acceptable salt or ester of Cucurbitine.

39. The method of claim 37, wherein Cucurbitine is present in laevorotatory form.

40. The method of claim 37, comprising administering Cucurbitine in a composition comprising from 0.001% to 10% by weight of said at least substantially pure Cucurbitine based on the total composition.

41. The method of claim 37, comprising administering Cucurbitine in a composition comprising from 0.01% to 10% by weight of said at least substantially pure Cucurbitine based on the total composition.

42. The method of claim 37, comprising administering Cucurbitine in a composition comprising from 0.01% to 5% by weight of said at least substantially pure Cucurbitine based on the total composition.

43. The method of claim 37, comprising administering Cucurbitine at least in part encapsulated in liposome vesicles.

44. The method of claim 37, wherein said Cucurbitine is selected from the group consisting of (−)Cucurbitine, Cucurbitine mono hydrobromide, Cucurbitine dihydrobromide, Cucurbitine mono hydrochloride, Cucurbitine dihydrochloride, Cucurbitine methyl ester and Cucurbitine ethyl ester.

45. The method of claim 37, wherein said skin is a dry skin.

46. The method of claim 37, wherein said skin is a sensitive skin.

47. The method of claim 1, wherein said treatment is selected from the group consisting of bronchial asthma, hayfever, spasmodic tracheitis, rhinitis, urticaria, eczema, red blotches, pruritus, Quincke's oedema, and allergic conjunctivitis.

* * * * *